United States Patent [19]

Knighton

[11] Patent Number: 5,165,938
[45] Date of Patent: Nov. 24, 1992

[54] WOUND HEALING AGENTS DERIVED FROM PLATELETS

[75] Inventor: David R. Knighton, Hudson, Wis.

[73] Assignees: Regents of the University of Minnesota, Minneapolis, Minn.; Curative Technologies, Inc., Setauket, N.Y.

[21] Appl. No.: 526,542

[22] Filed: May 18, 1990

Related U.S. Application Data

[63] Continuation of Ser. No. 39,776, Apr. 15, 1987, abandoned, which is a continuation of Ser. No. 786,206, Oct. 10, 1985, abandoned, which is a continuation-in-part of Ser. No. 676,471, Nov. 29, 1984, abandoned.

[51] Int. Cl.⁵ ............................................. A61K 35/14
[52] U.S. Cl. ........................................ 424/532; 514/2
[58] Field of Search ......................................... 424/532

[56] References Cited

U.S. PATENT DOCUMENTS

| | | |
|---|---|---|
| 3,628,974 | 12/1971 | Battista ................. 514/774 |
| 3,883,574 | 5/1975 | Axen . |
| 3,948,875 | 4/1976 | Cohen et al. . |
| 4,177,261 | 12/1979 | Dietze et al. . |
| 4,272,521 | 6/1981 | Zuffi . |
| 4,272,523 | 6/1981 | Kotitschke et al. . |
| 4,273,871 | 6/1981 | Tolbert et al. . |
| 4,287,180 | 9/1981 | Thomas . |
| 4,287,184 | 9/1981 | Young . |
| 4,294,826 | 10/1981 | Feldman . |
| 4,296,100 | 10/1981 | Franco . |
| 4,298,598 | 11/1981 | Schwarz et al. . |
| 4,350,687 | 9/1982 | Lipton et al. . |
| 4,378,347 | 3/1983 | Franco . |
| 4,427,650 | 1/1984 | Stroetmann . |
| 4,427,651 | 1/1984 | Stroetmann . |
| 4,431,582 | 2/1984 | Stenn . |
| 4,444,760 | 4/1984 | Thomas, Jr. . |
| 4,465,669 | 8/1984 | Wissler et al. . |
| 4,470,968 | 9/1984 | Mitra et al. . |
| 4,470,969 | 9/1984 | Pancham et al. . |
| 4,471,053 | 9/1984 | Comi et al. . |
| 4,479,896 | 10/1984 | Antoniades .................. 424/101 |
| 4,479,938 | 10/1984 | Thomas . |
| 4,503,038 | 5/1985 | Banda et al. . |
| 4,512,977 | 6/1985 | Lundy . |
| 4,514,387 | 6/1985 | Wissler . |
| 4,529,590 | 7/1985 | LeVeen et al. . |
| 4,621,052 | 11/1986 | Sugimoto . |
| 4,727,137 | 2/1988 | Bert Vallee et al. . |

FOREIGN PATENT DOCUMENTS

| | | |
|---|---|---|
| 0105014 | 4/1984 | European Pat. Off. . |
| 0128849 | 12/1984 | European Pat. Off. . |
| 0190018 | 8/1986 | European Pat. Off. . |
| 2472385 | 7/1981 | France . |
| 2533438 | 3/1984 | France . |
| 8701728 | 3/1987 | PCT Int'l Appl. . |
| 2146335A | 4/1985 | United Kingdom . |

OTHER PUBLICATIONS

Knighton et al.—Annals of Surgery vol. 196, No. 4 (Oct. 1982) pp. 379-388.
Grotendorst et al.—Surg. Sci. Serv (1984) 2 (Soft and Hard Tissue Repair) pp. 20-40.
Grotendorst—J. of Trauma—vol. 24 (9, Suppl) (1984) pp. 49-54.
Grotendorst—Chem. Abst. vol. 101 (1984) p. 208615r.
Michaeli et al.—Chem. Abst. vol. 102 (1985) p. 43765v.
B. Zetter & H. Antoniades; J. Supra Molecular Structure; 11:361-370 (1979).
Edited T. Hunt, et al.; "Role of Platelets in Wound Healing: Demonstration of Angiogenic Activity", Soft and Hard Tissue Repair, 380-394 (Praeger NY 198).
Edited J. Linman; "Hemorrhagic Disorders"; Hematology, 849-894 (McMillan 1975).
R. Senior, et al.; J. Cell Biology; 96:382-385 (Feb. 1983).
M. Sporn, et al.; Science; 219:1329-1331 (Mar. 1983).
T. Hunt; Frontiers in Understanding Burn Injury; 24(9) Supplement: S39-S46; (Sep. 1984).
"Role of Platelets and Fibrin in the Healing Sequence"by D. R. Knighton in Annals of Surgery, vol. 96, Oct. 1982.
"Isolation of a nonmitogenic angiogenesis factor from wound fluid" by Michael Banda et al. from Proc. Natl. Acad. Sci USA, vol. 79, Dec. 1982.
"Platelet-Derived Growth Factor is a Chemoattractant for Vascular Smooth Muscle Cells" by G. R. Grotendorst et al Journal of Cellular Physiology.
"Hemostasis and Blood Coagulation".
"Stimulation of Human Vascular Endothelial Cell Growth by a Platelet Derived Growth Factor and Thrombin", by Bruce Zetter and Harry Antoniades from Journal of Supermolecular Structure, 1979.

(List continued on next page.)

*Primary Examiner*—Sam Rosen
*Attorney, Agent, or Firm*—Dorsey & Whitney

[57] ABSTRACT

Platelet enriched plasma is produced from blood. The platelets are activated by thrombin which causes the release of platelet derived growth and angiogenesis factors. A carrier such as a microcrystalline collagen is added to produce a wound treating salve. The compound is applied directly to wounds and initiates healing in non-healing wounds as well as accelerating normal wound healing by increasing vascularization, stimulating fibroblast mitosis and migration and increasing collagen synthesis by fibroblasts. The process of treatment involves the use of a composition containing the materials released by platelets during the platelet release reaction.

12 Claims, No Drawings

OTHER PUBLICATIONS

"The Platelet-Drived Growth Factor", pp. 203-210.

"Radioimmunoassay of human serum growth factor for Balb/c-3T3 cells; Derivation from Platelets" by Antoniades et al. from vol. 74, Proc. Natl. Acad. Sci, U.S.A.

Time Magazine article of Oct. 7, 1985 on work done at Harvard Medical School.

"Stimulation of Granulation Tissue Formation by PDGF in Normal and Diabetic Rats", by Gary R. Grotendorst et al.

"Surgeon's Treatment Lets Patients heal Stubborn Wounds with Own Blood, from Mpls Star and Trib" Nov. 12, 1984.

Platelet-Derived Growth Factor: Identification of Constituent Polypeptide Chains by A. Johnsson, from Biochemical and Biophysical Research Communications.

Sederma Brochure: "Repair Factor F.C.P." (publication date unknown, but after 1986).

Greaves, Clin. Exp. Dermatol, 5:101-103 (1980).

Thornton et al., Burns, 8:156-160 (1981).

Frati et al., Exper. Eye Res., 14:135-141 (1972).

Carpenter, J Invest. Dermatol, 71:283-288 (1978).

Niall et al., J Surg. res. 33:164-169 (1982).

Deuel et al., Proc. Natl. Acad. Sci. USA, 78:4584-4587 (1981).

WOUND HEALING AGENTS DERIVED FROM PLATELETS

This application was made under contract with the Department of Veterans Affairs. Title to the invention remains with the inventor subject to the U.S. Government's reservation of a nonexclusive, irrevocable, royalty-free license in the invention with the power to grant sublicenses for all government purposes.

This application is a file wrapper continuation of co-pending application Ser. No. 07/039,776, filed Apr. 15, 1987 now abandoned which was a file wrapper continuation of co-pending application Ser. No. 06/786,206, filed Oct. 10, 1985, now abandoned, which was a continuation in part of co-pending application Ser. No. 06/676,471, filed Nov. 29, 1984, now abandoned.

FIELD OF THE INVENTION

This invention relates to wound healing agents, specifically angiogenic and growth factors, their production from blood and their use to facilitate the healing of wounds.

BACKGROUND OF THE INVENTION

Angiogenesis, which is the proliferation and directed growth of capillary endothelium, along with fibroplasia and collagen synthesis are integral components of a host's response to wounding. The activation of platelets and the clotting cascade are among the first reactions to injury.

Platelets activated by thrombin release a mitogen, or growth factor, for fibroblasts and smooth muscle cells and stimulate increased collagen synthesis by smooth muscle cells in vitro. The mitogen, (platelet-derived growth factor, hereinafter PDGF) is composed of two polypeptides. An article describing PDGF was published in 1982 by G. R. Grotendorst, T. Chang, H. E. J. Seppa, H. K. Kleinman and G. R. Martin in the *Journal of Cellular Physiology* entitled "Platelet-Derived Growth Factor is a Chemoattractant for Vascular Smooth Muscle Cells", Vol. 113, pp. 261-266. The article is incorporated herein by reference.

A non-mitogenic substance, called angiogenic factor, is also produced by thrombin activated platelets and stimulates capillary growth. Various angiogenesis factors are known including tumor, retinal and wound fluid angiogenesis factors. It is unknown whether all angiogenesis factors share a common mechanism of action upon capillary endothelial cells.

Angiogenesis factors were isolated and described by M. S. Banda, D. R. Knighton, T. K. Hunt and Z. Werb in *Proc. Nat'l. Acad. Sci. U.S.A.* (7773-7777, Dec. 1982), nn an article entitled "Isolation of a nonmitogenic angiogenesis factor from wound fluid", the disclosure of which is incorporated herein by reference.

Angiogenesis and platelet derived growth factors are described by D. R. Knighton, T. K. Hunt, K. K. Thakral and W. H. Goodson III, in "Role of Platelets and Fibrin in the Healing Sequence," Annals of Surgery 196: 379-388 (1982), the disclosure of which is incorporated by reference. In this article, the successful treatment of a non-healing wound in a patient is described in which a single, ten-unit platelet transfusion was given. The wound healed in three weeks.

A recent study has indicated that when the body's normal healing process works, it is only at about a 50% effectiveness level.

A human angiogenic factor is produced from human foreskin fibroblasts in Tolbert et al. U.S. Pat. No. 4,273,871. A publically available foreskin fibroblast cell line is utilized to produce an angiogenic factor. In Antoniades U.S. Pat. No. 4,479,896 the disclosure of which is incorporated herein by reference, platelet-derived growth factors are characterized and extracted for study by gel electrophoresis means.

BRIEF SUMMARY OF THE INVENTION

Thrombin activated platelets have the capacity to stimulate angiogenesis, increased collagen synthesis and cell division and growth. It has been found that samples of whole blood may be utilized to prepare a platelet-enriched plasma, which when activated by thrombin, contains angiogenic and growth factors which may be used to speed the healing process of wounds.

Blood is stabilized and centrifuged to obtain a platelet-rich plasma. The blood is stabilized by mixing with citrate-phosphate-dextrose in a ratio of 1:5 (20% solution). The platelet-rich plasma (hereinafter PRP) is preferably centrifuged again until a high concentration of platelets is obtained. The platelets are then placed in a platelet buffer. The concentration of platelets should be at least 1,000,000 platelets per milliliter. Preferably, the concentration should be on the order of 1,000,000,000 platelets per milliliter.

Thrombin is added to the PRP in order to activate the platelets. Preferably, about 1 to about 10 units of thrombin are utilized per milliliter of PRP. The thrombinactivated platelets release platelet derived growth factors (hereinafter PDGF) and platelet derived angiogenesis factors (hereinafter PDAF). The platlets and thrombin are allowed to incubate at room temperature for about 5 to 10 minutes.

The activated PRP containing PDGF and PDAF is preferably added to a biologically compatible macromolecular substance which acts as a carrier. First the platlets are centrifuged at about 950 × g and the platelet free supernatant is mixed with the carrier. Preferably, a microcrystalline collagen such as Avitene ® brand collagen as sold by FMC Corp., Avicel Dept., Marcus Hook, Pa. 19061 is utilized as the biologically compatible carrier. Microcrystalline collagens are biologically compatible in the body. Enough carrier is added to soak up all the platelet rich plasma that is obtained from the blood. For example, a 40 ml blood sample would typically require about 25 ml of carrier after enrichment. The paste so obtained is preferably stored on ice or in the refrigerator.

The pharmaceutical preparations for use as a wound dressing sold by Pharmacia Fine Chemicals, Inc. of Piscataway, N.J. under the trademark Debrisan is a suitable carrier.

The activated PRP within the carrier may then be applied to a wound. The highly enriched and active PDGF and PDAF therewithin assists in healing by proliferating and directing the growth of capillary endothelium, doubling the rate of collagen synthesis and by producing leukocyte chemotaxis. Mitogenic activity results in cellular division and growth to replace the lost tissue.

Daily application of the activated PRP to wounds stimulates and bolsters the healing sequence. The amount of PRP processed from 40 ml of blood is enough to produce applications for seven days. The material is placed over the entire wound at a relatively uniform thickness, approximately two millimeters thick. Granulation, contraction and epithelization may be initiated through the use of activated PRP where the body's own repair signals are inadequate to stimulate good healing.

Whenever thrombin is used herein, it is referring to thrombin as a biologic release agent for platelet release. Other biologic release agents known in the art, including collagen, ADP and serotonin, may be utilized instead of or in addition to thrombin to activate the platelets, although thrombin is preferred.

DETAILED DESCRIPTION OF THE INVENTION

Blood obtained from the individual to be treated with the wound healing factors of the invention is stabilized in siliconized tubes containing acid-citrate dextrose (0.15M citrate, 2% glucose, pH 4.2) (hereinafter CPD) and is centrifuged in order to separate out, the platelet-rich plasma therefrom. Forty to sixth milliliters of blood combined with 4-6 ml of CPD is then centrifuged at about 135 × g for 20 minutes at about 4° C to obtain platelet-rich plasma. The platelet rich plasma is removed and placed into another sterile, 50ml tube. A platelet count is then taken. The CDP is utilized to prevent activation of the clotting sequence by contact of the blood with the plastic in the syringe. The CPD is present in the syringe while the blood is withdrawn from the patient. The blood is continuously mixed with the CPD to prevent coagulation. The platelet-rich plasma in the tube is then centrifuged at 750 × g for 10 minutes at 4° C.

The platelet-free plasma is removed and discarded. The platelet pellet is resuspended in a quantity of platelet buffer to produce a final ml. A lower concentration of about a million platelets per ml is useful, but is less preferred. The platelet buffer utilized contains 0.05 M HEPES (N-2-hydroxyethylpiperazine-n-2-ethanesulfonic acid), 0.03 M glucose, 0.004 M KCl, 0.1 M NaCl and about 0.35% human serum albumin adjusted to a pH of about 6.5. A sample is frozen at about −20° C. for later testing of mitogenic activity. Another sample is streaked onto blood agar as a sterility test.

The platelet-rich plasma is the only blood fraction utilized in the processes and compositions of the invention. The PRP is then activated with purified thrombin at a rate of about 1 to about 10 units of thrombin per milliliter of PRP. Preferably, about 1 unit of thrombin per ml of platelet-rich plasma is utilized. The activity of the thrombin coagulates the fibrinogen and activates platelets causing them to release alpha granules containing platelet-derived growth factor and platelet-derived angiogenesis factor. The thrombin used was Thrombinar TM brand from Armour Pharmaceutical Co. of Kankakee, Ill. The platelets and thrombin are allowed to incubate at room temperature for about 5-10 minutes.

The PRP is then subjected to a removal of platelets and fibrin by centrifugation. The resulting supernatant contains both PDAF and PDGF after centrifuging at 950 × g for about 5 minutes at 4° C. The pellet is discarded since the PDAF & PDGF have been extracted into the supernatant. PDGF has been isolated and characterized. It is a protein of 30,000 molecular weight which breaks down into two molecular weight species of 15,000 and 14,000 molecular weight.

In order to apply the PDAF and PDGF in the platelet-free supernatant thus obtained to a wound, it is desirable to utilize a carrier substance which is biologically compatible and acts as a temporary "depot". A macromolecular substance such as microcrystalline collagen provides a suitable carrier. An especially preferred carrier is Avitene ® brand microcrystalline collagen from FMC Corp., Avicel Dept., Marcus Hook, Pa. 19061. The resultant composition is thicker and will tend to remain in position in contact with the wound. Debrisan TM brand wound dressing which contains Sepharose TM brand beads, trademarks of Pharmacia Fine Chemicals, Inc. of Piscataway, N.J., may be utilized as an alternative carrier. Preferably, about 8-10 ml of supernatant per gram of carrier is used to produce a paste.

Application of the wound treating composition is by physically applying the material over an into the wound as in applying a medicated salve. Treatments should be repeated on a daily basis as long as the wound remains open. A preferred treatment is to apply an approximately one mm thick dressing of the platelet factor/carrier complex to the wound in the morning. It is then dressed with a sterile, dry dressing. In the evening, the dressing is removed and the substance is removed by washing with sterile saline.

Although the clinical testing involving the wound treating compositions of the invention have been directed to wounds on the body exterior, the compositions may treat internal wounds as well. Sutures may be impregnated with the wound treating compositions to speed internal healing. The wound treating compositions may also be used in conjunction with biodegradable dressings, as a coating over implantable devices and biodegradable devices utilized in surgical procedures. Generally, any foreign body to be inserted into a patient may be coated with the composition to speed the healing process. Alternatively, the composition may be applied over the damaged tissue directly.

Initial clinical trials have been performed on eight patients, all with nonhealing wounds from periods of one to five years. All patients had maximal standardized care in attempts to heal the wounds. That therapy had failed. In all cases, administration of platelet-derived factors initiated a healing response as evidenced by granulation tissue formation (granulation tissue contains fibroblasts, endothelial cells and collagen). The wounds closed by contraction and epithelialization or by skin grafting. Stimulation of healing and eventual repair occurred in all applications.

While it is preferred to prepare activated PRP for wound treatment purposes directly from the injured animal's own blood, the advantages of the invention may be achieved by using blood or outdated platelets from animals of the same species. Utilization of blood from the injured individual to be treated is especially preferred since it avoids exposure to possible hepatitis or other contaminants from banked blood. The use of a patient's own blood would also eliminate any possible allergic reactions. A consistent source of the material may be obtained from washed, outdated human platelets. The substances may also be utilized in veterinary applications by utilizing platelets derived from the animal itself or another animal within the same species.

EXAMPLE I

A patient having an open wound on the left foot following debridement of dead tissue and transmetatarsal amputation was started on PDGF and PDAF obtained as described above from his own blood. After the treatment protocol, the wound was filled with new granulation tissue. A subsequent debridement showed completely covered metatarsal bones and contracture of the sizable wound.

EXAMPLE II

A patient underwent amputation of his right great toe and was treated with standard therapy for three weeks without any granulation tissue accumulating within the wound. He was then started on the platelet factor therapy of the invention. After three weeks of treatment, the wound contracted approximately 30–40% and was healing rapidly.

EXAMPLE III

A patient having two large wounds on the medial and lateral aspect of his transmatatarsal amputation stump had been treated for four months without healing using conventional therapy. Within two weeks of treatment with PDAF and PDGF as described above, the wound had cleared of an apparent infection and started producing granulation tissue.

Thirty-eight nonhealing ulcers from 28 diabetic patients were treated with the PRP paste. The average duration of the ulcers before treatment was 6½ years. A paste prepared from PRP at a concentration of about $10^9$ platelets/ml was combined with Avitene brand collagen. The patients applied the PDGF and PDAF containing paste daily for 12 hour periods for an average of 8 weeks. Each day, the wounds were debrided of dead tissue. All of the wounds produced granulation tissue and closed an average of 83% when compared to starting wound area. Ninety-five percent of the ulcers were successfully treated resulting in either total wound epithlialization or successful skin grafting. Only two of these nonhealing wounds did not heal. The healed ulcers remain closed with no evidence of hypertrophic scar formation orneoplastic formation.

In considering this invention, it should be remembered that the disclosure is illustrative only, and that the scope of the invention should be determined by the appended claims.

What is claimed is:

1. A process for treating damaged, live, animal tissue which comprises applying over the damaged tissue an effective amount of a treating composition containing the materials released by platelets during the platelet release reaction and facilitating healing of the damaged tissue.

2. The method of claim 1 wherein the materials are applied topically in an amount sufficient to cause migration and/or division of fibroblast cells, capillary endothelial cells and/or epithelial cells.

3. The method of claim 1 wherein said platelets are isolated from blood prior to release of the materials.

4. The method of claim 1 wherein said tissue is mammalian tissue.

5. The method of claim 4 wherein said tissue is human tissue.

6. The method of claim 1 wherein said platelets are mammalian platelets.

7. The method of claim 6 wherein said platelets are human platelets.

8. The method of claim 7 wherein prior to release of the materials said platelets were removed from the person whose tissue is being treated.

9. The method of claim 7 wherein prior to release of the materials said platelets were removed from a person or persons other than the person whose tissue is being treated.

10. The method of claim 1 wherein the materials are released from said platelets by use of an activator selected from the group consisting of thrombin, adenosine diphosphate and collagen.

11. The method of claim 10 wherein said activator is thrombin.

12. A process for treating a wound of a live animal which comprises applying over the wound an effective amount of a treating composition containing the materials released by platelets during the platelet release reaction and facilitating healing of the wound.

* * * * *